US00PP22235P2

(12) United States Plant Patent
Tsukahara

(10) Patent No.: US PP22,235 P2
(45) Date of Patent: Nov. 8, 2011

(54) ***PETUNIA* PLANT NAMED 'BLUETTE STRAWBERRY SUNDAE RS'**

(50) Latin Name: ***Petunia* hybrid**
Varietal Denomination: Bluette Strawberry Sundae RS

(76) Inventor: Jun Tsukahara, Yame (JP)

( * ) Notice: Subject to any disclaimer, the term of this patent is extended or adjusted under 35 U.S.C. 154(b) by 0 days.

(21) Appl. No.: 12/660,100

(22) Filed: Feb. 18, 2010

(51) Int. Cl.
*A01H 5/00* (2006.01)

(52) U.S. Cl. ..... Plt./356

(58) Field of Classification Search ..... Plt./356
See application file for complete search history.

*Primary Examiner* — Kent L Bell

(57) ABSTRACT

A new and distinct *Petunia* cultivar named 'Bluette Strawberry Sundae RS' is disclosed, characterized by pink and white fully double bi color flowers, mounding and floriferous plant habit. The new variety is a *Petunia*, suitable as an outdoor garden or container plant.

1 Drawing Sheet

Latin name of the genus and species: *Petunia* hybrid.

Variety denomination: 'Bluette Strawberry Sundae RS'.

The new *Petunia* cultivar resulted as part of a planned breeding program by the inventor Jun Tsukahara, in Yame, Fukuoka, Japan. The objective of the breeding program was to develop new *Petunia* varieties with interesting colors and attractive plant forms.

The new variety resulted from the crossing of the seed parent, an unnamed, unpatented proprietary *Petunia* seedling with the pollen parent, an unnamed, unpatented proprietary *Petunia* seedling in September 2005. The new variety was discovered in November of 2007 by the inventor in a group of seedlings resulting from that crossing, in a commercial greenhouse in Yame, Fukuoka, Japan.

Asexual reproduction of the new cultivar 'Bluette Strawberry Sundae RS' by was first performed by vegetative cuttings at a commercial greenhouse in Yame, Fukuoka, Japan in January 2008. Subsequently many generations have been produced and have shown that the unique features of this cultivar are stable and reproduced true to type.

SUMMARY OF THE INVENTION

The cultivar 'Bluette Strawberry Sundae RS' has not observed under all possible environmental conditions. The phenotype may vary somewhat with variations in environment such as temperature, day length and light intensity, without however, any variance in genotype.

The following traits have been repeatedly observed and are determined to be the unique characeristics of 'Bluette Strawberry Sundae RS.' These characteristics in combination distinguish 'Bluette Strawberry Sundae RS' as a new and distinct *Petunia* cultivar:

1. Unique and stable pink and white bi color flower.
2. Compact and mounding plant shape.
3. Highly floriferous habit.
4. Fully double flower.

COMPARISON TO THE PARENT VARIETIES

Plants of the new cultivar 'Bluette Strawberry Sundae RS' are similar in most horticultural characteristics to plants of the unnamed proprietary seed parent. However, the seed parent has a solid pink colored flower, which are single, not double, and smaller overall flower size than the new cultivar. Additionally, the seed parent has thinner diameter stems than 'Bluette Strawberry Sundae RS'.

Plants of the new cultivar 'Bluette Strawberry Sundae RS' are similar in most horticultural characteristics to plants of the unnamed proprietary pollen parent. However, the pollen parent has solid purple colored flowers, a larger overall flower size than the new cultivar. Additionally, the pollen parent produces taller plants than 'Bluette Strawberry Sundae RS'.

COMPARISON TO COMMERCIAL VARIETIES

The new cultivar can be compared to the commercial variety 'KLEPH06126' U.S. Plant Pat. No. 19,907. 'Bluette Strawberry Sundae RS' is similar to this commercial variety in most horticultural characteristics, however, the new variety forms more mound shape, less trailing plants, and has a different color.

BRIEF DESCRIPTION OF THE PHOTOGRAPH

The accompanying photograph illustrates in full color a typical plant of 'Bluette Strawberry Sundae RS' grown in a greenhouse, in a 24 cm basket. Age of the plant photographed is approximately 4 months from 5 rooted cuttings. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurement describe 'Bluette Strawberry Sundae RS' plants grown in a commercial greenhouse in Oxnard, Calif. The growing temperature ranged from 18° C. to 25° C. The greenhouse is subject to partial shade. General light conditions are bright, normal sunlight with some shade during the brightest part of the day. Measurements and numerical values represent averages of typical plant types.

Botanical classification: *Petunia* hybrid 'Bluette Strawberry Sundae RS'

PROPAGATION

Time to initiate roots: About 7 days at approximately 25° C.
Time to develop roots: About 14 to 21 days at approximately 25° C.
Root description: Fine, fibrous.

PLANT

Growth habit: Mounding.
Pot size of plant described: Approximately 6 inch.
Age of plant described: Approximately 12 weeks from a rooted cutting.
Height: Approximately 18 cm from soil line to top of plant.
Plant spread: Approximately 67 cm at widest point.
Growth rate: Rapid.
Branching characteristics: Free branching.
Length of primary lateral branches: Approximately 28 cm.
Quantity of primary lateral branches: Approximately 30
Characteristics of primary lateral branches:
*Diameter.*—Approximately 0.4 cm.
*Color.*—Near RHS Yellow-Green 144B.
*Texture.*—Pubescent.
*Strength.*—Very strong.
Internode length: Approximately 2.5 cm.

FOLIAGE

Leaf:
*Arrangement.*—Opposite.
*Quantity.*—Approximately 20 per main lateral branch.
*Average length.*—Approximately 4.8 cm.
*Average width.*—Approximately 2.9 cm.
*Shape of blade.*—Ovate.
*Apex.*—Acute.
*Base.*—Obtuse.
*Margin.*—Entire.
*Texture of top surface.*—Matte with very slight pubescence.
*Pubescence.*—Very short, less than 1 mm hairs, sparsely covering leaf.
*Aspect.*—Flat to slightly recurved.
*Color.*—Young foliage upper side: Near RHS Green 137A. Young foliage under side: Near RHS Green 137C. Mature foliage upper side: Near RHS Green 137A. Mature foliage under side: Near RHS Green 137C.
*Venation.*—Type: Pinnate. Venation color upper side: Near RHS Green 143C. Venation color under side: Near RHS Green 143C.
*Petiole.*—Length: Approximately 0.8 cm. Diameter: Approximately 0.2 cm. Color: Near RHS Green 143C. Texture: Pubescent.

FLOWER

Natural flowering season: Spring and Summer
Days to flowering from rooted cutting: Approximately 50.
Inflorescence and flower type and habit: Singly occurring at leaf axils, fully double flowers with fused petals.
Rate of flower opening: Approximately 2 to 3 days from bud to fully opened flower.
Flower longevity on plant: Approximately 5 days.
Approximate quantity of flowers per plant: Approximately 200 flowers and buds.
Persistent flowers:
Flower size:
*Diameter.*—Approximately 4 cm.
*Flower measurements.*—Individual tube not measurable because filled with petals.
*Petal quantity.*—Approximately 15, irregularly sized and fused.
*Texture.*—Smooth.
*Apex.*—Acute.
*Margin.*—Entire.
Color:
*When opening.*—Inner surface: Near RHS Red-Purple 70B. Outer surface: Near RHS Red-Purple 70C.
*Fully opened.*—Inner surface: Near RHS Red-Purple 70C with streaks near White N155B. Outer surface: Near RHS Purple 70D. Petal color, fading to: Near RHS Red-Purple 70C with streaks near White N155B.
Bud:
*Shape.*—Ovate.
*Length.*—Approximately 1.5 cm.
*Diameter.*—Approximately 1 cm.
*Color.*—Near RHS Green 143B.
Calyx/sepals:
*Quantity per flower.*—5, fused at base.
*Shape.*—Oblanceolate.
*Length.*—Approximately 1.6 cm.
*Width.*—Approximately 0.6 cm.
*Apex.*—Obtuse.
*Base.*—Fused.
*Margin.*—Entire.
*Texture.*—Pubescent.
*Color.*—Upper Surface: Near RHS Green 137A. Lower Surface: Near RHS Green 137C.
Peduncle: Length: Approximately 1.6 cm. Diameter: Approximately 0.2 cm. Color: Near RHS Green 144B. Orientation: Approximately 45 degree angle from stem.
Fragrance: Sweet.

REPRODUCTIVE ORGANS

Stamens:
*Number.*—5.
*Filament length.*—Approximately 0.6 cm.
Anthers: Length: Approximately 0.1 cm. Shape: Oblate. Color: RHS White 155C. Pollen: Not observed.
Pistil:
*Number.*—1.
*Length.*—Approximately 0.8 cm.
*Style.*—Length: Approximately 0.6 cm. Color: Near RHS Green 143C.
*Stigma.*—Shape: Linear. Color: Near RHS Yellow-Green 145D. Ovary Color: Near RHS Yellow-Green 145C.

OTHER CHARACTERISTICS

Seeds and fruits: Not observed.
Disease/pest resistance: Neither resistant nor susceptible to normal diseases and pests of *Petunia*.
Temperature tolerance: The new variety tolerates temperatures between approximately 6° to 35° C.

What is claimed is:

1. A new and distinct cultivar of *Petunia* plant named 'Bluette Strawberry Sundae RS' as herein illustrated and described.

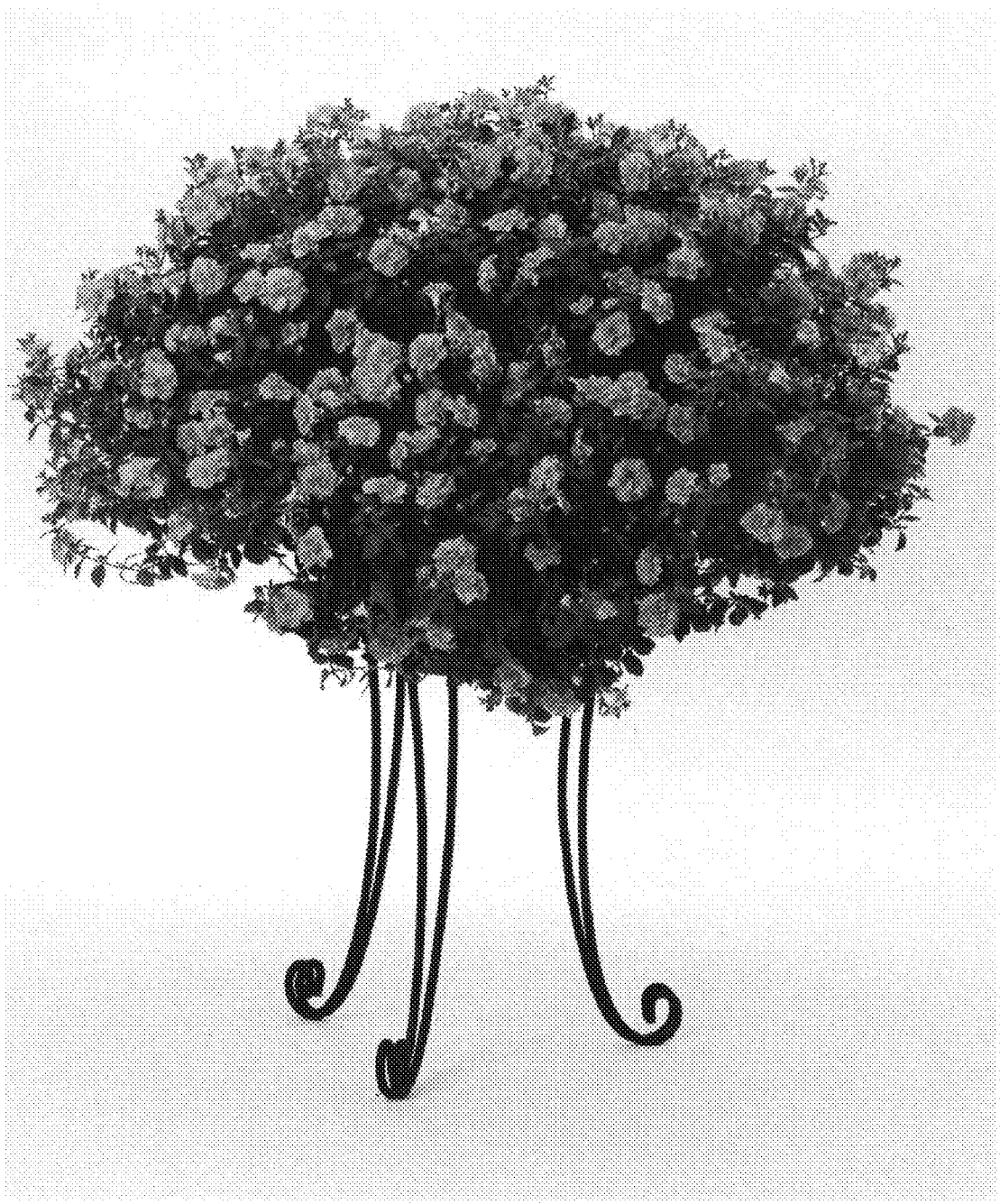

* * * * *